(12) United States Patent
Gigler et al.

(10) Patent No.: US 9,599,557 B2
(45) Date of Patent: Mar. 21, 2017

(54) DUST LINE WITH OPTICAL SENSOR, AND METHOD FOR MEASURING THE COMPOSITION OF DUST

(71) Applicant: SIEMENS AKTIENGESELLSCHAFT, Munich (DE)

(72) Inventors: Alexander Michael Gigler, Untermeitingen (DE); Holger Hackstein, Dietzenbach (DE); Remigiusz Pastusiak, Munich (DE); Kerstin Wiesner, Hoehenkirchen-Siegertsbrunn (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 14/770,663

(22) PCT Filed: Feb. 11, 2014

(86) PCT No.: PCT/EP2014/052594
§ 371 (c)(1),
(2) Date: Aug. 26, 2015

(87) PCT Pub. No.: WO2014/131611
PCT Pub. Date: Sep. 4, 2014

(65) Prior Publication Data
US 2016/0003736 A1    Jan. 7, 2016

(30) Foreign Application Priority Data
Feb. 26, 2013  (DE) .................. 10 2013 203 109

(51) Int. Cl.
*G01N 21/47* (2006.01)
*G01N 21/53* (2006.01)
(Continued)

(52) U.S. Cl.
CPC ......... *G01N 21/53* (2013.01); *G01N 15/0205* (2013.01); *G01N 15/0612* (2013.01);
(Continued)

(58) Field of Classification Search
CPC ........... G01N 15/0205; G01N 15/0612; G01N 2015/0096; G01N 2021/151;
(Continued)

(56) References Cited

U.S. PATENT DOCUMENTS 3,628,028 A   12/1971 Thorsheim
3,975,084 A   8/1976 Block
(Continued)

FOREIGN PATENT DOCUMENTS

AT   405 216 B      6/1999
CN   202013208 U   10/2011   ............. G01D 21/02
(Continued)

OTHER PUBLICATIONS

International Search Report mailed May 26, 2014 in related International Application No. PCT/EP2014/052594; 3 pages.

*Primary Examiner* — Tri T Ton
(74) *Attorney, Agent, or Firm* — Slayden Grubert Beard PLLC

(57) ABSTRACT

An optical sensor is arranged in an indentation of a dust line, the indentation being equipped with at least one gas inlet nozzle for removing the dust from the optical sensor. Dust is transported through the dust line. An optical property of the dust is measured using at least one optical sensor arranged in an indentation of the dust line, and the dust is then removed from the optical sensor by blowing in air using the at least one gas inlet nozzle arranged in the indentation.

15 Claims, 2 Drawing Sheets

(51) Int. Cl.
*G01N 21/15* (2006.01)
*G01N 21/85* (2006.01)
*G01N 15/06* (2006.01)
*G01N 15/02* (2006.01)
*G01N 33/24* (2006.01)
*G01N 21/3554* (2014.01)
*G01N 21/3563* (2014.01)
*G01N 21/552* (2014.01)
*G01N 21/35* (2014.01)
*G01N 21/84* (2006.01)
*G01N 15/00* (2006.01)

(52) U.S. Cl.
CPC ......... *G01N 21/15* (2013.01); *G01N 21/8507* (2013.01); *G01N 33/24* (2013.01); *G01N 21/3554* (2013.01); *G01N 21/3563* (2013.01); *G01N 21/474* (2013.01); *G01N 21/552* (2013.01); *G01N 2015/0096* (2013.01); *G01N 2021/151* (2013.01); *G01N 2021/3595* (2013.01); *G01N 2021/536* (2013.01); *G01N 2021/8411* (2013.01); *G01N 2021/8528* (2013.01)

(58) Field of Classification Search
CPC ..... G01N 2021/3595; G01N 2021/536; G01N 2021/8411; G01N 2021/8528; G01N 21/15; G01N 21/3554; G01N 21/3563; G01N 21/474; G01N 21/53
USPC .... 356/445–448, 237.1–237.6, 239.1–239.8, 356/241.1–241.6, 335–343
See application file for complete search history.

(56) References Cited

U.S. PATENT DOCUMENTS

| | | |
|---|---|---|
| 4,583,859 A | 4/1986 | Hall, II |
| 7,869,028 B2 | 1/2011 | Mannhardt et al. |
| 2008/0212087 A1 | 9/2008 | Mannhardt et al. |
| 2010/0059669 A1 | 3/2010 | Jamaluddin et al. |
| 2010/0328663 A1 | 12/2010 | Parks et al. |
| 2012/0154161 A1 | 6/2012 | Knox et al. |

FOREIGN PATENT DOCUMENTS

| | | |
|---|---|---|
| DE | 44 26 088 A1 | 3/1995 |
| DE | 102010019076 A1 | 11/2011 |
| DE | 10 2013 203 109.2 | 2/2013 |
| GB | 2 391 940 A | 2/2004 |
| WO | 03/060480 A1 | 7/2003 |
| WO | 2004/031742 A1 | 4/2004 |
| WO | 2006/087546 A1 | 8/2006 |
| WO | 2009/060358 A2 | 5/2009 |
| WO | PCT/EP2014/052594 | 2/2014 |

DUST LINE WITH OPTICAL SENSOR, AND METHOD FOR MEASURING THE COMPOSITION OF DUST

CROSS-REFERENCE TO RELATED APPLICATIONS

This application is based on and hereby claims priority to International Application No. PCT/EP2014/052594 filed on Feb. 11, 2014 and German Application No. 10 2013 203109.2 filed on Feb. 26, 2013, the contents of both of which are hereby incorporated by reference.

BACKGROUND

Described below is a dust line for transporting dust, having at least one optical sensor for monitoring a property of the dust. Also described below is a method for measuring a property of dust in a dust line.

Dust lines are used in a number of automated processes for transporting dust, wherein the dust is either transported in a targeted manner to the location of use thereof or else transported away from the location of production thereof. Below, dust is understood to mean an accumulation of solid particles, the particle diameter of which is significantly below 1 mm, usually below 100 μm. Dust swirling in air can levitate for a long time and it can therefore be transported, even in whirled-up form, together with an air flow by way of pneumatically operated dust lines. The most important application of such dust lines is found in coal power plants, in which finely ground coal dust with a particle diameter of usually at most 0.5 mm is fed to a burner by way of a dust line. However, there are also other automated processes in which amounts of dust are transported by way of dust lines, for example when supplying flour, cocoa or starch in food production or when removing wood dusts and metal dusts in material processing.

Monitoring the composition of the transported dusts is desirable for many such processes. For reasons of quality control and of monitoring the processes, a measurement and a monitoring of mean particle dimensions, moisture content and other chemical compositions may be relevant. When supplying coal dust in a coal power plant, the calorific value of the coal in particular is an important parameter that should be monitored. The calorific value is a measure of the energy released during combustion per unit mass of fuel. For coal dust, the calorific value depends, inter alia, on the moisture of the coal dust, on the chemical composition of the coal particles and on the particle dimension of the coal dust. During the operation of a power plant, all these parameters should be kept within a predetermined process window, wherein the predetermined process window may also vary in time, for example if the nominal power of the power plant changes throughout the day.

In principle, monitoring the dust properties by optical measuring processes is desirable. However, it is very difficult to perform optical measurements within a dust line since an optical probe within the line is exposed to high wear-and-tear. Very strong abrasion occurs at the walls of dust lines, particularly when transporting coal dust, and so an optical measurement probe with a sensitive optical window is damaged very quickly. All that is known is an option for a reflection measurement, in which a measurement probe is installed flush with the inner wall of the dust line. However, the wear-and-tear is also great in this case. Cleaning or replacing the probe is very difficult and complicated under normal process conditions. Since, in principle, all combustible dusts such as coal dust, wood dust, flour, cocoa, starch and cellulose dust are explosive, such a dust line may be operated in an explosion-protected manner. This precludes regular cleaning, servicing or the replacement of an optical measurement probe, as well as the use of some other measurement methods, for example electric measurement methods within the dust line.

SUMMARY

In one aspect, a dust line for transporting dust is specified, the dust line having at least one optical sensor. In another aspect, a method for measuring a property of dust in a dust line is specified.

The dust line for transporting dust in an automated process has at least one optical sensor for monitoring a property of the dust. The optical sensor is arranged in an indentation of the dust line, wherein the indentation is equipped with at least one gas inlet nozzle for removing the dust from the optical sensor.

The dust line renders it possible to transport, e.g. pneumatically, the dust through the line and, in the process, monitor the composition of the dust by an optical measurement during the ongoing process. Arranging the optical sensor in an indentation in the dust line reduces the wear-and-tear of the sensor since it is not exposed directly to the abrasive forces in the main channel of the transport flow. Rather, the measurement takes place in a mechanically protected region of the transportation line. During the dust transportation through the line, the indentation in the dust line is largely filled by dust. This filling corresponds to automated taking of a sample of the transport flow. After measuring optical parameters with the optical sensor, this sample volume can be emptied again by virtue of the at least one gas inlet nozzle of the dust line being put into operation in order to largely free the indentation from dust by blowing in air. The sensor surface exposed thus is subsequently available again for a further measurement. The dust line configured thus renders it possible to perform repeated measurements of the optical parameters of the dust in a simple manner, in order thereby to determine the composition and further properties of the dust and, for example, monitor the adherence to a predetermined process window. A further aspect of the dust line is that the measurement of the optical parameters can be conducted in a contactless manner, meaning that the dust line can be designed as an explosion-protected surrounding. This is important, particularly for combustible dusts such as coal dust, flour, cocoa, starch and cellulose dust. Moreover, the dust line is low maintenance due to the low abrasion of the optical sensor in the indentation in the dust line.

In the method for measuring a property of dust in a dust line, dust is transported through a dust line. An optical property of the dust is measured by at least one optical sensor arranged in an indentation of the dust line. Subsequently, the dust is removed from the optical sensor by blowing in air with at least one gas inlet nozzle arranged in the indentation. The aspects of the method emerge analogously to the aspects of the dust line.

The optical sensor can be a sensor for measuring a reflection, having at least one probe body and an optical window. Here, the probe body acts as a support for the optical measurement arrangement and the optical window forms the interface between the optical sensor and the sample volume to be measured, i.e. the dust contained in the indentation. A reflection property may be measured since most dusts are hardly transparent in the range of infrared light and visible light but have a relatively high reflection coefficient at some wavelengths. The optical window and the probe body may be separated from one another, for example in order to replace and/or clean these components independently of one another in the case of possible wear-and-tear, because wear-and-tear and/or dirtying of the components of the optical sensor may occur, even in the protected environment within the indentation in the case of constant operation.

The optical sensor may include at least one light source for emitting light into the optical window, at least one photodetector for measuring light and at least one optical waveguide. Here, the at least one optical waveguide serves to forward the light from the light source to the optical window and to guide the light to be measured from the optical window to the photodetector. In one embodiment, wavelength ranges for the optical measurement are the visible part of the spectrum and the infrared range, or in the near infrared range (NIR) between 780 nm and 3 μm and the mid-infrared range (MIR) between 3 μm and 50 μm. When measuring in the infrared range, the at least one optical waveguide may include fluoride fibers and/or sapphire fibers. The optical sensor can also include two or more optical waveguides.

The optical sensor can include at least one element for splitting light into the spectral components thereof. This element can be e.g. a grating or prism. Particularly when using visible light, the element may already split the light between the light source and the optical window into the spectral components thereof and/or to select specific spectral ranges for coupling into the optical window. Alternatively or additionally, the light between the optical window and the photodetector, decoupled again, can be decomposed into the spectral constituents thereof in order to enable a wavelength-selective measurement.

Alternatively or additionally, the optical sensor can include at least one element for establishing by calculation the spectral components of light by way of a Fourier analysis, such as when using infrared light. The element for establishing the spectral components by calculation can be e.g. an interferometer, which splits the light emitted by the light source into two individual beams with a beam splitter, which beams interfere with one another. The path length of one of the partial beams is continuously modified in the process such that a measurement signal is obtained at the detector as a function of this path length. By way of a Fourier transform of the obtained interferogram it is possible to determine the spectral components of the light by calculation.

A plurality of gas inlet nozzles can be arranged in the indentation of the dust line. These gas inlet nozzles can be embodied in such a way that they are capable of blowing air or any other noninflammable gas into the indentation at at least two different angles in relation to a transportation direction of the dust. The use of a plurality of gas inlet nozzles and blowing gas in from a plurality of different angles renders it possible to free the indentation and the optical sensor arranged therein, in particular the optical window, from dust in a particularly reliable and reproducible manner. Even if one of the gas inlet nozzles fails, one or more further nozzles can still reliably free the indentation from dust. In one embodiment, the gas inlet nozzles are not operated simultaneously, but rather to blow gas in alternately in turn in the case of a plurality of nozzles. This prevents the generation of turbulence and enables reliable cleaning by a controlled feed of the deposited dust into the transport flow in the dust line.

The optical sensor can be a sensor suitable for measuring the attenuated total internal reflection of light in the sample window. The process of attenuated total internal reflection (also referred to as ATR spectroscopy) is a measurement process, in which radiation is guided by total reflection in an optical window with a high refractive index. A sample to be examined, which is brought into contact with, or into very close spatial vicinity to, the optical window, can then attenuate the total reflection within the optical window. The attenuation is based on the interaction of the evanescent electromagnetic field of the light with the sample, wherein the range of this interaction is of the order of the light wavelength. In this embodiment, such a light sensor can therefore substantially measure dust particles which lie directly on the optical window. The attenuation of the total internal reflection of the light is particularly strong for those spectral regions in which there is an absorption by the sample to be measured. Characteristic bands are measured in these spectral regions in the case of a spectrally resolved measurement, which enable deductions to be made about the chemical composition of the sample to be examined. The particle size of dust particles to be examined also influences the extent of the attenuation of the total internal reflection and therefore the strength of the measured spectral bands.

For measuring the attenuated total internal reflection, the refractive index of the optical window maybe greater than 1.5, or even greater than 2. Suitable materials for such optical windows are e.g. diamond, sapphire, germanium, zinc selenide, silver halides, fused quartz, silicon, thallium bromoiodide or germanium arsenic selenide. The form of the optical window may be configured such that a plurality of reflections occur on the outer interface of the optical window in the beam path of the light, i.e. attenuation of the total internal reflection as a result of an optical interaction with the sample to be examined may occur at a number of points on the optical window. To this end, the optical window may be configured in the form of a prism.

Alternatively, the optical sensor can be a sensor suitable for measuring the diffuse reflection of light at the dust. In this embodiment, light is decoupled from the optical window into the interior of the indentation. The light is diffusely reflected at the dust particles to be measured and a certain portion thereof is coupled back into the optical window and guided via one of the optical waveguides to the photodetector. For the measurement of the diffuse reflection at the dust, an optical window may be made of material which has a refractive index that is as low as possible, for example less than 2, so that the light can be decoupled into the interior of the indentation.

The aforementioned method operations can be repeated a plurality of times in order to monitor an automated process. By way of example, the repetition can be implemented periodically. Only regular repetition of the measurement of the optical properties of the dust enables continuous monitoring of an ongoing process, for example a check whether a predetermined process window with predetermined process parameters is adhered to. Regulating such process parameters is also only made possible by such an ongoing repetition of the optical measurement.

The optical property of the dust can be the attenuation of the total internal reflection of light in an optical window of the optical sensor as a result of deposited dust.

Alternatively, the optical property of the dust can be the diffuse reflection of light at dust contained in the indentation.

The optical property of the dust can be measured as a function of the wavelength of light emitted by a light source of the optical sensor. Such a measurement method may be used, in particular, if the chemical composition of the dust is a relevant measurement parameter because a spectrally resolved evaluation of the optical property of the dust enables a direct assignment to known substances by way of a comparison with catalogued spectral band positions, bandwidths and band intensities of known substances and known mixtures. Furthermore, a predetermined process window can also be defined in such a way that only a specific predetermined deviation from a predefined ideal spectrum may be tolerated. Process parameters may be corrected if a deviation that is greater than permitted is measured in any region of the spectrum.

It is also possible to determine the particle size of the dust with the aid of the measurement of the optical property of the dust. By way of example, a mean effective particle dimension can be determined from the extent of the attenuation of the total internal reflection since many small dust particles bring substantially more matter into optical interaction with evanescent waves of the light in the optical window than a few large dust particles.

It is also possible to determine the chemical composition of the dust with the aid of the measurement of the optical property of the dust. Monitoring the chemical composition is easily possible by, in particular, analyzing the spectral dependence of the optical property. One aspect which may be particularly relevant here is the monitoring of the moisture content of the dust, i.e., for example, the measurement of the water component bound to the surface of the dust particles or else the measurement of structurally bound water. This is possible in a particularly simple manner with the aid of the well-known absorption bands of water in the infrared range of the spectrum.

The automated process to be monitored can be the supply of coal dust in a coal power plant. The adherence to a predetermined process window can be monitored and/or regulated with the aid of the measurement of the optical property of the coal dust.

BRIEF DESCRIPTION OF THE DRAWINGS

These and other objects and advantages of the present invention will become more apparent and more readily appreciated from the following description of the preferred embodiments, taken in conjunction with the accompanying drawings, in which.

DETAILED DESCRIPTION OF THE PREFERRED EMBODIMENTS

Reference will now be made in detail to the preferred embodiments of the present invention, examples of which are illustrated in the accompanying drawings, wherein identical or functionally identical elements are provided with the same reference signs in the figures if not otherwise indicated.

Figure 1:
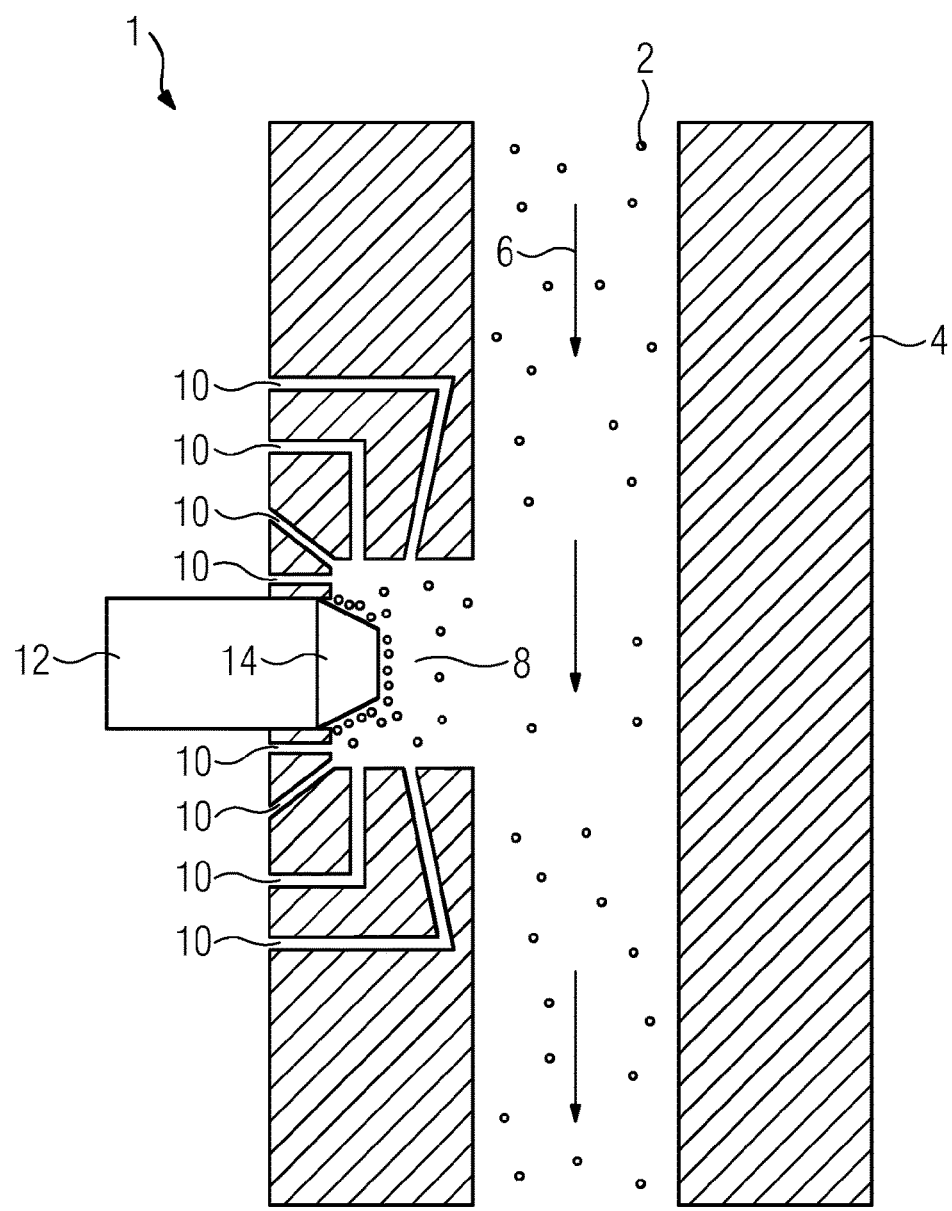
FIG. 1 is a side view of a cross section of the dust line according to a first exemplary embodiment.

FIG. 1 shows a schematic cross section of a dust line 1 according to a first exemplary embodiment. What is shown is a section of the dust line 1, which contains an optical sensor 15 for monitoring the dust 2, the sensor being reproduced in FIG. 1 by the probe body 12 and the optical window 14 thereof. The optical sensor 15 is arranged in an indentation 8 of the dust line 1. The dust line 1 serves to transport dust 2 along a transportation direction 6. In the exemplary embodiment, the dust line 1 is a line for transporting coal dust to a combustion system in a power plant. Here, the coal dust is produced at the same location as the combustion system in a pulverizer. However, alternatively, it can also be delivered already in dust form. The chemical composition of the coal dust, in particular the moisture and calorific value of the coal, should be checked continuously during the supply of the coal dust in order to ensure that the combustion system operates within the desired process window and fulfills the electric nominal power of the power plant. This electric nominal power may vary throughout the day, which makes repeated readjustment and monitoring of the process parameters necessary. Even in the case of a constant nominal power of the power plant, quality variations in the calorific value of the coal dust can be compensated for by other parameters, e.g. a modified mass flow, such that the overall heating power remains constant. The measured data in respect of the chemical composition can furthermore serve to check the quality of the initial substances, i.e. the rough coal. Measured data in relation to the mean particle dimension of the coal dust can moreover serve as control variables when setting the parameters of the upstream pulverizer. In the shown exemplary embodiment, the coal power plant is a power plant for hard coal dust. However, alternative examples with power plants for lignite dust and hard coal dust are conceivable. Combined power plants, in which hard coal dust or lignite dust can be combusted alternatively, are also feasible; determining and monitoring the coal type used at a respective time is particularly important in these. The subject matter likewise relates to dust lines which transport dust-shaped initial products to a machine in industrial production processes, for example flour, cocoa or starch in food production. Alternatively, dusts, which are produced as waste products during processes in material processing, e.g. wood or metal dusts in sawing or grinding plants, may be transported away in a similar dust line. Here, monitoring of the dust parameters by the optical measurement may serve, for example, the end of continuously monitoring these waste products for polluting substances or substances hazardous to health, or else to monitor the process parameters of the material processing process.

In the first exemplary embodiment shown in FIG. 1, the dust 2 collects in the indentation 8 of the dust line during the transport. In particular, the dust collects on the optical window 14, enabling an optical measurement of the dust parameters. After an optical measurement of the dust properties, the indentation 8 is largely freed from dust 2 again by virtue of air being blown into the indentation 8 through the gas inlet nozzles. The gas inlet nozzles are realized as purge air nozzles 10 here. However, it is also possible to use different noninflammable gases for cleaning the optical window 14. In the shown exemplary embodiment, eight purge air nozzles 10 are arranged around the optical window 14 in such a way that the different surfaces of the window 14 are cleaned in succession by pressurized air from different angles of incidence and hence there is removal of the dust 2 from the indentation 8 that is as complete as possible. After cleaning using purge air, the air flow is switched off. The indentation can once again be filled with dust and a new measurement value can be established. By way of example, the measurement can be repeated in each case after a few seconds. Alternatively, the purge air nozzles can also be arranged asymmetrically. By way of example, it is also possible to arrange a single purge air nozzle in such a way that it blows the air flow in the direction of the dust line.

In FIG. 1, the finely distributed dust particles 2 should only be understood schematically. In a process for supplying dust coal, the dust particles 2 will in actual fact be transported through the line with a substantially denser concentration. However, what will often be the case is that an even more densely packed collection of dust particles 2 is deposited in an indentation 8 than in the actual transportation tube, which is reproduced in FIG. 1 by the outer wall 4 thereof. Measuring the dust property within the indentation makes the measurement result relatively independent of the process-dependent variation in the density of the dust stream in the transportation line. What is important for a reproducible repetition of the measurement conditions is that the packing density of the dust particles 2 is comparable between measurements. Moreover, the form and dimensions of the indentation 8 in this case have an influence on the amount of dust 2 deposited per measurement cycle, the reproducibility of the dust collection prior to a measurement and the possibility of reproducible cleaning of the indentation 8. By way of example, the indentation 8 can have a cylindrical form and have a width of approximately 3 to 30 mm and a depth of 3 to 30 mm. Here, the aspect ratio, i.e. the ratio between width and depth of the indentation, can be greater than or less than 1. As an alternative to a cylindrical indentation 8, other forms are also conceivable, for example an arched form, a square form, part of a conical form or a trapezoidal form.

Figure 2:
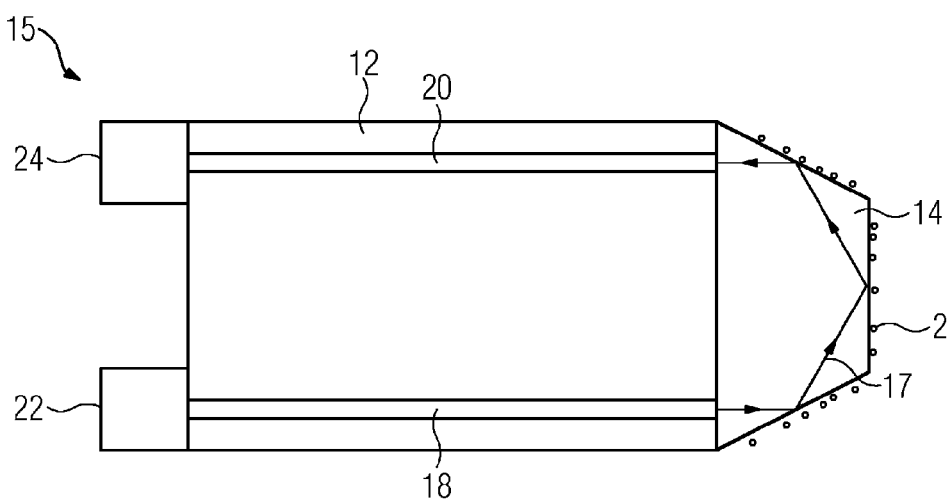
FIG. 2 is a plan view of the optical sensor according to the first exemplary embodiment.

A schematic detailed view of the optical sensor 15 used in the first exemplary embodiment is shown in FIG. 2. This optical sensor operates according to the principle of attenuated total reflection. In this case, infrared radiation from a light source 22 is coupled into the optical window 14 by a first optical waveguide 18. The optical window 14 has a trapezoidal cross section in this example, leading to the infrared light in an exemplary beam path 17 being reflected at three faces of the outer side of the optical window 14. At the employed light wavelength, the material of the optical window 14 has a refractive index above 2. In this example, the optical window is manufactured from zinc selenide. In any case, the refractive index of the optical window 14 is so high that, in the case of a typical beam path 17, the light undergoes total reflection at the inner side of the window 14. However, if dust 2 is densely deposited on the surface of the optical window 14, there can be interaction between the dust and evanescent waves of the light, and the total internal reflection is particularly attenuated for those wavelengths for which there is a strong absorption of the radiation in the dust particle. The remaining totally reflected radiation 17 is guided by a second optical waveguide 12 through the probe body 12 to a photodetector 24. The signal measured by the optical sensor 12 is forwarded to a readout unit (not shown here). The light source 22 can emit monochromatic or polychromatic light. In the case of polychromatic light, an element (not shown here) for splitting the light into the spectral components thereof and/or for selecting one of these components may additionally be present. Alternatively, an interferometer can be arranged in the beam path in such a way that a computational calculation of the individual wavelength components, in particular of the attenuated total reflection, as a function of the wavelength is possible.

Figure 3:
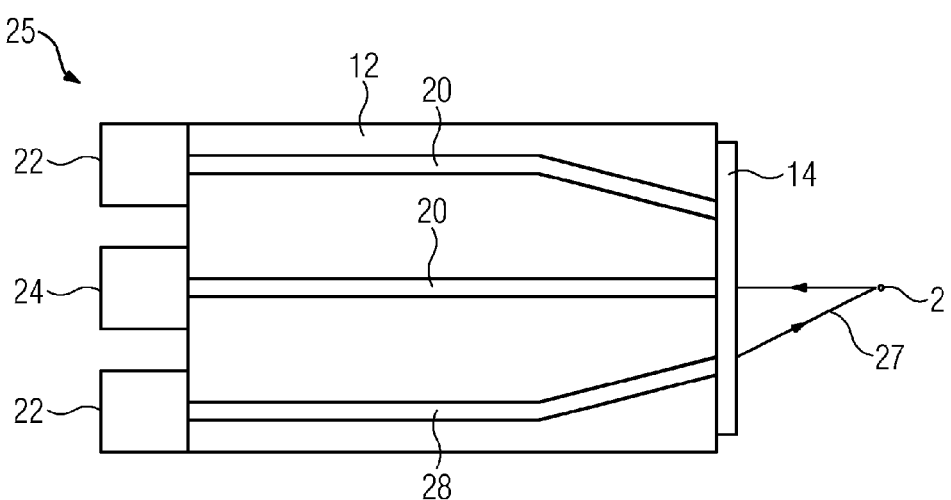
FIG. 3 is a plan view of the optical sensor according to a second exemplary embodiment.

FIG. 3 shows an alternative embodiment of an optical sensor 25 in accordance with a second exemplary embodiment. In this case, the arrangement of the indentation 8 and the purge air nozzles 10 in the dust line 1 is to be analogous to the first exemplary embodiment shown in FIG. 1. The optical sensor 25 operates according to the principle of diffuse reflection. To this end, e.g. two light sources 22 are arranged in such a way that the radiation thereof is coupled through two optical waveguides 20 and 28 into the optical window 14. The optical window 14 is made of a material with a refractive index of below 1.6; in this example, it is made of fused quartz. The light from the light source is visible light in this case, which is decoupled from the optical window 14 along an exemplary beam path 27 and can be diffusely reflected by a dust particle 2 situated in the vicinity. In the case of diffuse reflection, a broad angle distribution of the reflected light emerges and the angle of reflection does not necessarily equal the angle of incidence. Parts of the reflected light can be captured by the second optical waveguide and guided to the optical sensor 25. Here, it is also possible to select the wavelength of the light using additional elements (not shown here). The optical measurement can be performed successively for different wavelengths in the spectral range of the light source or a simultaneous measurement of all wavelengths with an interferometric measurement is possible. In any case, it is possible to establish the strength of the diffuse reflection as a function of the wavelength, enabling a measurement of the material-dependent absorption properties of the dust 2, and also the dust density and/or the mean particle size.

Both exemplary embodiments render it possible to continuously monitor the properties, such as chemical composition, moisture and particle dimension, of the dust by regularly repeated measurements and regulate associated process parameters using the measurement signals. This embodiment of the dust line 1 enables measurements in explosion-protected surroundings with low wear-and-tear of the optical sensors 15, 25.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide* v. *DIRECTV*, 69 USPQ2d 1865 (Fed. Cir. 2004).

The invention claimed is:

1. A dust line for transporting coal dust when supplying coal dust in a coal power plant, comprising:
    at least one optical sensor disposed in a recess-like indentation of the dust line for collecting coal dust, the optical sensor monitoring a chemical composition of the coal dust by measuring an optical property of the coal dust; and
    at least one gas inlet nozzle disposed in the indentation, the gas inlet nozzle configured to remove the coal dust from the optical sensor and from the indentation after the optical property of the coal dust has been measured.

2. The dust line as claimed in claim 1, wherein the optical sensor is a sensor for measuring a reflection and includes at least one probe body and an optical window.

3. The dust line as claimed in claim 2, wherein the optical sensor includes:
    at least one light source configured to emit light into the optical window;
    at least one photodetector configured to measure light; and
    at least one optical waveguide.

4. The dust line as claimed in claim 2, wherein a plurality of gas inlet nozzles are disposed in the indentation in the dust line, the gas nozzles being configured to blow air into the indentation at at least two different angles in relation to a surface of the optical window.

5. The dust line as claimed in claim 1, wherein the optical sensor includes at least one element configured to split light into spectral components and calculate the spectral components of the light by a Fourier analysis.

6. The dust line as claimed in claim 1, wherein the optical sensor measures an attenuated total internal reflection of light in the optical window.

7. The dust line as claimed in claim 1, wherein a refractive index of the optical window is at least 1.5.

8. The dust line as claimed in claim 1, wherein a refractive index of the optical window is at least 2.0.

9. The dust line as claimed in claim 1, wherein the optical sensor measures a diffuse reflection of light on the coal dust.

10. A method for measuring a property of coal dust in a dust line, comprising:
- transporting coal dust through a dust line;
- measuring an optical property of the coal dust with at least one optical sensor disposed in a recess-like indentation of the dust line;
- removing the coal dust from the optical sensor by blowing air through at least one gas inlet nozzle disposed in the indentation;
- monitoring a supply of the coal dust in a coal power plant;
- analyzing a spectral dependence of the optical property of the coal dust; and
- monitoring a chemical composition of the coal dust.

11. The method as claimed in claim 10, wherein the optical property of the coal dust is an attenuation of a total internal reflection of light in an optical window of the optical sensor as a result of deposited coal dust.

12. The method as claimed in claim 11, further comprising:
- monitoring an adherence to a predetermined process window; and
- regulating the adherence based on the optical property of the coal dust.

13. The method as claimed in claim 10, wherein the optical property of the coal dust is a diffuse reflection of light by coal dust disposed in the indentation.

14. The method as claimed in claim 10, further comprising measuring the optical property of the coal dust as a function of a wavelength of light emitted by a light source as received by the optical sensor.

15. The method as claimed in claim 10, further comprising determining a particle size of the coal dust by measuring the optical property of the coal dust.

* * * * *